United States Patent [19]

Nambu

[11] Patent Number: 4,939,757

[45] Date of Patent: Jul. 3, 1990

[54] APPARATUS FOR DIAGNOSING PULMONARY VENTILATION FUNCTION

[75] Inventor: Kyojiro Nambu, Tochigi, Japan

[73] Assignee: Kabushiki Kaisha Toshiba, Kawasaki, Japan

[21] Appl. No.: 348,141

[22] Filed: May 2, 1989

Related U.S. Application Data

[63] Continuation of Ser. No. 33,629, Apr. 3, 1987, abandoned.

[30] Foreign Application Priority Data

Apr. 10, 1986 [JP] Japan ................................ 61-83333

[51] Int. Cl.$^5$ .............................................. A61B 6/00
[52] U.S. Cl. ........................................ 378/8; 378/95; 378/99; 358/111
[58] Field of Search ........................ 378/4, 8, 95, 99; 364/414; 128/716, 721, 722–724; 358/111

[56] References Cited

U.S. PATENT DOCUMENTS

| | | | |
|---|---|---|---|
| 3,974,386 | 8/1976 | Mistretta et al. | 378/99 |
| 3,993,995 | 11/1976 | Kaplan et al. | 378/8 |
| 4,387,722 | 6/1983 | Kearns | 378/95 |
| 4,689,670 | 8/1987 | Okazaki | 378/8 |

FOREIGN PATENT DOCUMENTS 0037722 10/1981 United Kingdom .................... 378/4

OTHER PUBLICATIONS

Herbert, David L., et al. *Mapping of Human Local Pulmonary Ventilation by Xenon Enhanced Computed Tomography*, Journal of Computer Assisted Tomography, 6(6):1088–1093 Dec. 1982.

Gur, David, et al., *Regional Pulmonary Ventilation Measurements by Xenon Enhanced Dynamic Computed Tomography: An Update*, Journal of Computer Assisted Tomography 5(5) 678–683, Oct. 1981.

*Primary Examiner*—Carolyn E. Fields
*Assistant Examiner*—David P. Porta
*Attorney, Agent, or Firm*—Finnegan, Henderson, Farabow, Garrett and Dunner

[57] ABSTRACT

An apparatus for diagnosing a pulmonary ventilation function includes a flow sensor for detecting a breathing cycle of a patient, a gas regulator for supplying a gaseous contrast medium to the patient, and a CT scanner for performing X-ray scanning and photography of a patient's lungs during one breathing cycle, in response to an output signal from the flow sensor and for outputting a plurality of tomographic images including X-ray absorbance components (CT value information components). The tomographic images generated by the CT scanner are stored in an image file memory. The CT value of the tomographic image read out from the image file memory is compared with a threshold value, and a region required for checking the pulmonary ventilation function is extracted as a result of comparison. The extracted region is displayed on a monitor.

10 Claims, 3 Drawing Sheets

APPARATUS FOR DIAGNOSING PULMONARY VENTILATION FUNCTION

This application is a continuation of application Ser. No. 07/033,629, filed Apr. 3, 1987 now abandoned.

BACKGROUND OF THE INVENTION

The present invention relates to an apparatus for diagnosing a pulmonary ventilation function.

If a pulmonary function is not performed normally, as in the case of a pulmonary invalid, the pulmonary function is examined to clarify the cause of the pulmonary invalid. At this time, a vital capacity is measured. Alternatively, the lungs are functioning rapidly, and a vital capacity during rapid functioning of the lungs is measured. Using these measurements, a doctor can diagnose the type and location of pulmonary invalid such as a bridle disorder or an obliterative disorder.

It is, however, difficult to precisely locate that portion of a lung which is not ventilated normally. As a result, the ventilation state of the lung cannot be quantitatively analyzed.

SUMMARY OF THE INVENTION

It is an object of the present invention to provide an apparatus for diagnosing a pulmonary ventilation function, so as to accurately examine that portion of lungs which is not ventilated normally.

According to the present invention, an apparatus is provided for diagnosing a pulmonary ventilation function, comprising a sensor for detecting a stop timing in which breathing changes from an inspiratory cycle to an expiratory cycle, and means for initiating scanning of a region of interest and the supply of a gaseous contrast medium, in response to an output from the sensor. The inspiratory cycle is started upon the supply of the gaseous contrast medium. Scanning continues from the start of inspiration to the end of expiration, so as to obtain several tomographic images. The supply of the gaseous contrast medium is terminated at the end of the expiratory cycle, and the tomographic images are stored in an image memory. Based on these stored tomographic images, the abnormal pulmonary portion is discriminated from the normal, healthy, portion according to the CT values of the portions containing the gaseous contrast medium. Stated more precisely, a portion containing the gaseous contrast medium has a higher X-ray absorbance than one not containing the gaseous contrast medium. A larger absorbance results in a larger CT value. The gaseous contrast medium does not enter the abnormal pulmonary portion, thus resulting in a low CT value and hence the locating of the abnormal portion.

DETAILED DESCRIPTION OF THE PREFERRED EMBODIMENT

Figure 1:
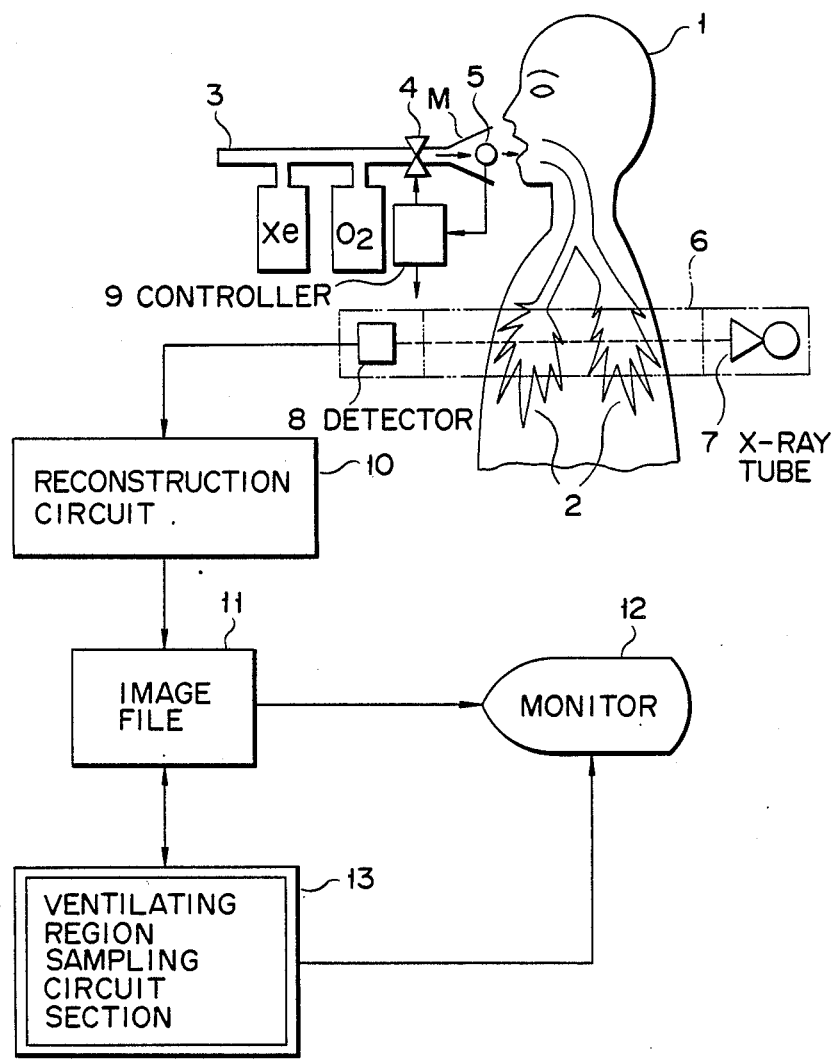
FIG. 1 is a schematic diagram of an apparatus for diagnosing a pulmonary ventilation function according to an embodiment of the present invention.

Referring to FIG. 1, gas regulator 3 is provided to supply a desired gaseous contrast medium such as an inert gas (e.g., xenon and krypton) to lungs 2 of patient 1. The flow rate of the gaseous contrast medium is controlled by valve 4. Flow sensor 5 is arranged in mask M, to detect the flow rate of the gaseous contrast medium supplied through valve 4.

X-ray CT device 6 comprises X-ray tube 7 and X-ray sensor 8 arranged at a position opposite thereto. Lungs 2 are located between tube 7 and sensor 8. Controller 9 is connected to valve 4 and X-ray CT device 6. When a desired amount of gaseous contrast medium is supplied, controller 9 controls CT device 6 to pick up a tomographic image. CT device 6 uses a high-speed X-ray CT scanner to pick up, one after another, 10 tomographic images, for example, during one breathing cycle while the gaseous contrast medium is being supplied to lungs 2.

The output stage of X-ray sensor 8 in X-ray CT device 6 is connected to reconstruction circuit 10. The output stage of reconstruction circuit 10 is connected to image file memory 11 for storing reconstructed information. Memory 11 is connected to ventilating region sampling circuit section 13, in order to extract a ventilating region, to enable a portion containing the gaseous contrast medium to be distinguished from other portions in the tomographic images.

Figure 2:
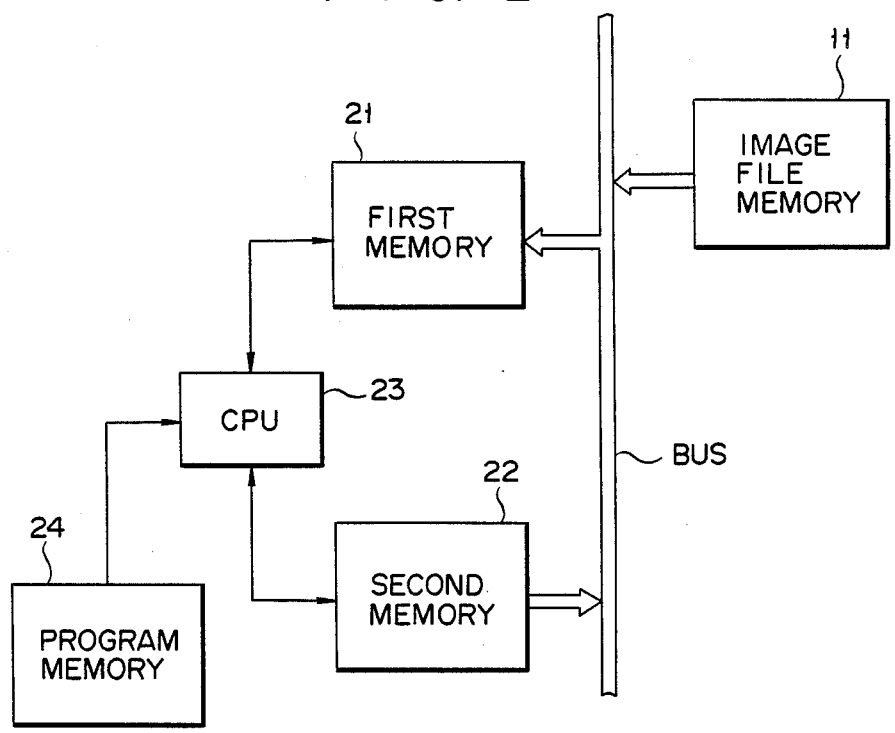
FIG. 2 is a block diagram of an expiratory region pick-up circuit section shown in FIG. 1.

Ventilating region sampling circuit section 13 includes first and second memories 21 and 22 connected to image file memory 11 via a bus, as is shown in FIG. 2. Image data is transferred from file 11 to memory 21, and is stored therein. Memory 22 stores CT values each extracted on the basis of two threshold values. Memories 21 and 22 are connected to CPU 23. CPU 23 controls read/write access and comparison between a CT and a threshold value according to programs read out from program memory 24.

The operation of the apparatus for diagnosing a pulmonary ventilation function will now be described.

Figure 3:
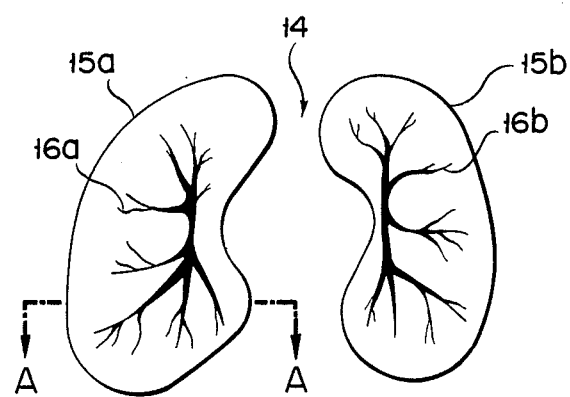
FIG. 3 is a longitudinal sectional view of the lungs.

When the gaseous contrast medium is not supplied from gas regulator 3 to lungs 2, and lungs 2 are photographed by X-ray CT device 6, a detection signal is output from X-ray sensor 8 and is input to reconstruction circuit 10. The detection signal is processed by reconstruction circuit 10, and the processed signal is stored in image file 11. Lungs 2 are angularly scanned by rotary scanning of X-ray CT device 6, and pulmonary tomographic image 14, shown in FIG. 3, is obtained and is stored in file 11. Tomographic image 14 shows left lung image 15a and right lung image 15b. Capillary blood vessels 16a and 16b and bronchi are shown in left and right lung images 15a and 15b, respectively.

Figure 4:
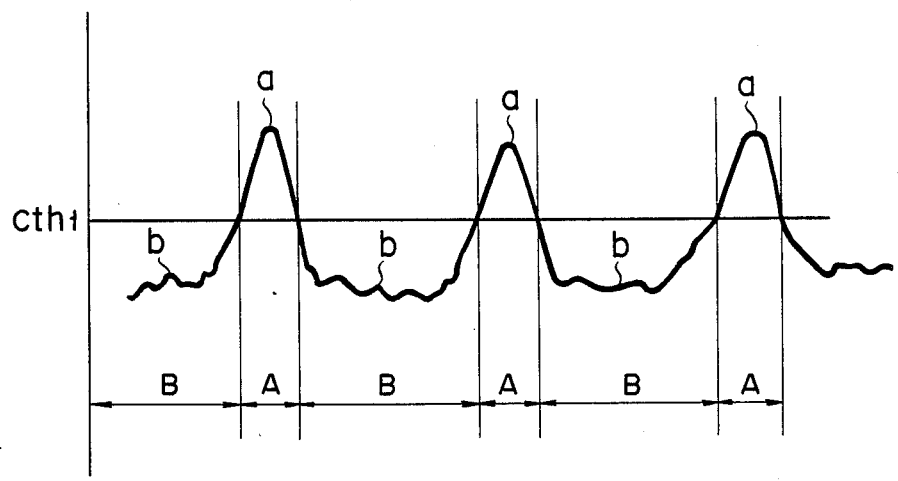
FIGS. 4 and 5 are graphs showing the CT value distributions, respectively.

An image in image file memory 11 is sent to ventilating region sampling circuit section 13. In this case, image information of the left lung, taken along the line A—A is stored in first memory 21 in circuit section 13. The A—A image information represents a distribution of X-ray absorbances (CT values), as shown in FIG. 4. In the CT value distribution, peaks a represent blood vessel portions, respectively. Other portions b represent alveoli and inner portions of bronchi.

CT values are sequentially read out from first memory 21 in units of pixels, and are compared with first threshold value $C_{th1}$ under the control of CPU 24.

Value Cth1 is determined to be a value for allowing extraction of portions b necessary for examining the ventilation function. The pixels having CT values larger than value Cth1 are eliminated, and those having CT values smaller than value Cth1 are stored in second memory 22. The above operation is repeated to eliminate CT values A corresponding to peak portions a. In other words, only CT value information, i.e., B corresponding to portions b is stored in memory 22.

Figure 5:
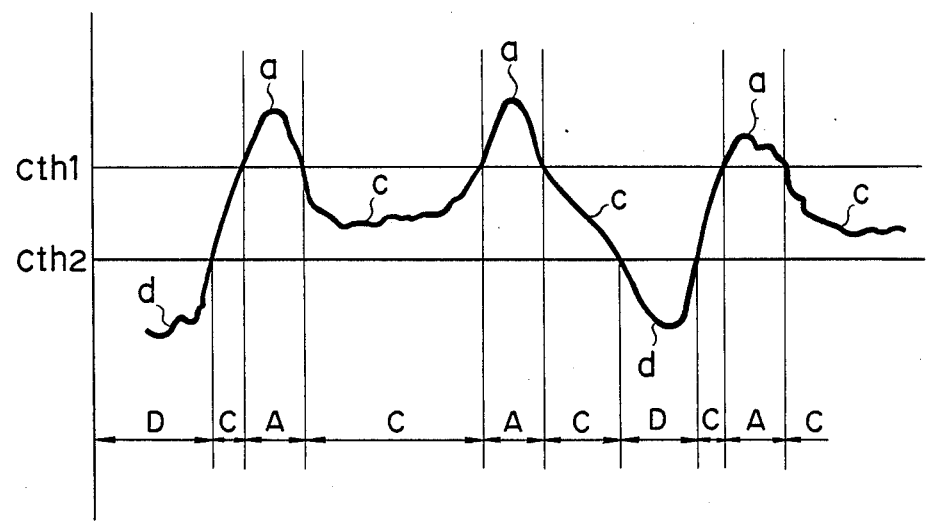

A gaseous contrast medium is supplied from gas regulator 3 to a patient. When the patient starts to inspire the gaseous contrast medium, the lungs are photographed a plurality of times by X-ray CT device 6, for example, 10 times. Ten tomographic images are then stored in image file memory 11. The CT values taken along the line A—A after inspiration of the medium are sequentially read out in units of pixels. The CT values are plotted to constitute a CT value distribution, as is shown in FIG. 5. The distribution shows portions c whose CT values are increased upon inspiration of the gaseous contrast medium, and portions d whose CT values are not changed by inspiration of the gaseous contrast medium. Portions c represent portions which are normally ventilated. Portions d represent portions which are not ventilated normally or disordered.

The CT values after inspiration of the gaseous contrast medium are supplied to CPU 23 in units of pixels, and are compared with second threshold value Cth2 representing an intermediate value between the CT value of the gaseous contrast medium and the CT value of air. Therefore, the CT values are classified into CT value information C corresponding to portions c and CT value information D corresponding to portions d. CT value information C represents portions containing the gaseous contrast medium, and CT value information D represents portions containing air.

The above classification method results in the A region portion (the blood vessel portion), the C region portion (the portion containing the gaseous contrast medium) and the D region portion (the portion containing air). When these regions are image-processed, in order to display an image on monitor 12, according to different colors and/or different brightness levels, the pixels constituting each region are counted to measure the area of each region.

Another mode of operation for detecting CT value will now be described below.

The end of the expiratory cycle of patient 1 is detected by flow sensor 5. In response to the end of the expiratory cycle, i.e, in response to a detection signal from flow sensor 5, X-ray CT device 6 initiates scanning of lungs 2. The images of lungs 2 are picked up by X-ray CT. The picked-up images are sequentially processed by reconstruction circuit 10, and the processed images are stored in image file memory 11. In this state, patient 1 begins an inspiratory cycle. The start of the inspiratory cycle is detected by flow sensor 5, and a gaseous contrast medium such as xenon gas is supplied through valve 4 to patient 1, in response to the detection signal from flow sensor 5. Patient 1 then inspires xenon gas. During this inspiratory cycle, scanning of lungs 2 continues to pick up pulmonary tomographic images, which are then stored in image file memory 11.

Scanning continues until the inspiratory cycle becomes the expiratory cycle and the expiratory cycle is completed. Photographed images are sequentially stored in image file memory 11. When flow sensor 5 detects the end of the expiratory cycle, controller 9 closes valve 4 in response to the detection signal from flow sensor 5. At this time, when a predetermined period of time has elapsed, controlled 9 instructs X-ray CT device 6 to end its scanning.

The CT values of the respective portions of lungs 2 are examined on the basis of a plurality of tomographic images obtained by rotary scanning during one breathing cycle, as described above. The CT value derived from a predetermined slice of the tomographic image is compared with first and second threshold values Cth1 and Cth2, in order to classify the image into three regions A, C, and D, as shown in FIG. 5. These regions are image-processed and the resultant image is displayed on monitor 12, in the form of different colors and/or different brightness levels. By counting the number of pixels constituting each region (A, C, and D) of the image, the area of each region can be digitally displayed.

As has been described above, by using a high-speed scanner to continuously pick up a plurality (e.g., 10 tomographic images, in this case) of tomographic images during one breathing cycle, i.e., a cyle in which the gaseous contrast medium is inspired into lungs 2, pulmonary ventilation can be continuously displayed on monitor 12. Therefore, the portion of at least one of the lungs which is normally ventilated can be accurately detected. In addition, the lungs can be dynamically and anatomically examined. The pulmonary ventilation function can be quantitatively analyzed. A large number of resultant tomographic images can be stored in the image file memory, and reproduced, as and when required.

I claim:

1. An apparatus for diagnosing the pulmonary ventilation function of the lungs of the patient, comprising:
    a. detecting means for detecting the breathing cycle of said patient;
    b. contrast-medium supply means for supplying, in response to said detecting means, a gaseous contrast medium to said patient for inspiration into said lungs;
    c. scanning means for CT-scanning said patient during one breathing cycle in response to said detecting means to obtain tomographic image data representing a plurality of images of said lungs;
    d. storage means for storing said image data;
    e. means for dectecting CT values of the stored image data for at least two of said images and comparing said CT values with at least one predetermined CT value which corresponds to the CT value of image data of a blood vessel to identify image data which corresponds to blood vessels;
    f. means for distinguishing said image data with CT values which exceed said at least one predetermined CT value from the rest of said image data to thereby distinguish said image data corresponding to blood vessels; and
    g. means for displaying at least one tomographic image from said image data, together with an indication of said areas of said lungs which correspond to said blood vessels.

2. An apparatus according to claim 1, wherein said contrast-medium supply means comprises means for feeding the gaseous contrast medium, said feeding means being provided with an outlet portion and with valve means arranged at said outlet portion of said feeding means to open and close in response to said breathing cycle detecting means, and said scanning means comprises a CT scanner for performing rotary scanning of the lungs.

3. An apparatus according to claim 2, wherein said scanner comprises a high-speed CT scanner for obtaining at least 10 tomographic images during one breathing cycle.

4. An apparatus according to claim 1, wherein said means for detecting CT values comprises first memory means for storing first tomographic image data corresponding to one tomographic image, means for reading out said one tomographic image data from said first memory means in units of pixels having CT values, comparing said CT values of said pixels with a first reference predetermined CT value and with a smaller second reference predetermined CT value, an classifying said one tomographic image data into first, second, and third regions depending on whether said CT values of said image data are greater than said first reference CT value, less than said first reference CT value and greater than said second reference CT value, and less than said second reference CT value, and second memory means for selectively storing the first, second, and third regions classified by said classifying means, and for causing said display means to display the information stored in said second memory means.

5. An apparatus according to claim 4, wherein said display means comprises means for displaying image data corresponding to the first, second, and third regions, in the form of different colors.

6. An apparatus according to claim 4, wherein said display means comprises means for displaying image data corresponding to the first, second, and third regions, in the form of different brightness levels.

7. An apparatus according to claim 1, wherein said means for detecting CT values comprises first memory means for storing first tomographic image data corresponding to one tomographic image, means for reading out said one tomographic image data from said first memory means in units of pixels having CT values, means for comparing said CT value of said pixels with a first reference predetermined CT value and a second, greater reference predetermined CT value, and selecting said one tomographic image with CT values less than said first reference CT value and greater than said second reference CT value, second memory means for storing the selected tomographic image data, and means for causing said display means to display the information stored in said second memory means.

8. An apparatus for diagnosing the pulmonary ventilation function of the lungs of a patient, comprising:
   a. contrast-medium supply means for supplying a gaseous contrast medium to said patient for inspiration into said lungs;
   b. scanning means for CT-scanning said patient to obtain tomographic image data of said lungs after inspiration of said gaseous contrast medium into said lungs;
   c. means for storing said image data;
   d. means for detecting CT values of said stored image data and comparing said CT values with at least one predetermined CT value which corresponds to the CT value of image data of a blood vessel; and
   e. means for eliminating said image data with CT values which exceed said at least one predetermined CT value to thereby eliminate said image data corresponding to blood vessels.

9. An apparatus of claim 8 including means for displaying a tomographic image from said remaining image data together with an indication of said areas of said lungs which fail to ventilate normally.

10. An apparatus according to claim 8, wherein said detecting means comprises a flow sensor arranged in a mask attached to the patient.

* * * * *